United States Patent [19]

Coville et al.

[11] Patent Number: 5,000,923
[45] Date of Patent: Mar. 19, 1991

[54] APPARATUS FOR RECEIVING A TEST SPECIMEN AND REAGENT

[75] Inventors: William E. Coville, Levittown, Pa.; Hyman Grossman, Lambertville, N.J.

[73] Assignee: Bio/Data Corporation, Hatboro, Pa.

[21] Appl. No.: 255,908

[22] Filed: Oct. 11, 1988

Related U.S. Application Data

[60] Continuation-in-part of Ser. No. 43,113, Apr. 27, 1987, Pat. No. 4,818,493, which is a division of Ser. No. 793,376, Oct. 31, 1985, Pat. No. 4,695,430.

[51] Int. Cl.⁵ .............. B01L 3/00; G01N 35/00; G01N 35/04
[52] U.S. Cl. .................... 422/102; 422/58; 422/61; 422/100; 422/101; 422/104
[58] Field of Search ............ 422/58, 61, 63, 64, 422/65, 67, 72, 73, 100, 102, 101, 104; 364/499; 210/651

[56] References Cited

U.S. PATENT DOCUMENTS

| | | | |
|---|---|---|---|
| 3,504,376 | 3/1970 | Bednar et al. | 23/230 |
| 3,645,690 | 2/1972 | Rochte et al. | 23/230 |
| 3,932,131 | 1/1976 | Rolfo-Fontana | 23/230 |
| 4,257,862 | 3/1981 | Schnipelsky et al. | 204/195 |
| 4,338,279 | 6/1982 | Orimo et al. | 422/64 |
| 4,343,705 | 8/1982 | Legg | 210/637 |
| 4,549,952 | 10/1985 | Columbus | 422/100 |
| 4,663,126 | 5/1987 | Gould et al. | 422/58 |
| 4,695,430 | 9/1987 | Coville et al. | 422/63 |
| 4,818,493 | 4/1989 | Coville et al. | 422/61 |

Primary Examiner—Robert J. Warden
Assistant Examiner—Kimberly A. Trautman
Attorney, Agent, or Firm—Seidel, Gonda, Lavorgna & Monaco

[57] ABSTRACT

An improvement to an apparatus for receiving a sample of biological fluid containing non-fluid components. Prior art sample cell for use in conjunction with prior art analytical apparatus comprises two slidably engaged members, first member comprising a reservoir for holding fluid sample to be tested, second member adapted to receive fluid from an external filter in one section and adapted to receive reagent and exhibit reaction in another section. The improvement comprises means for preventing smearing of fluid when members are moved relative to each other. A channel collects overflow from reservoir in first member, conducting overflow to a barrier placed in gap between first and second member. A wiper shears excess fluid from behind barrier, generally out of gap between first and second member, when the first and second members are moved relative to each other.

8 Claims, 5 Drawing Sheets

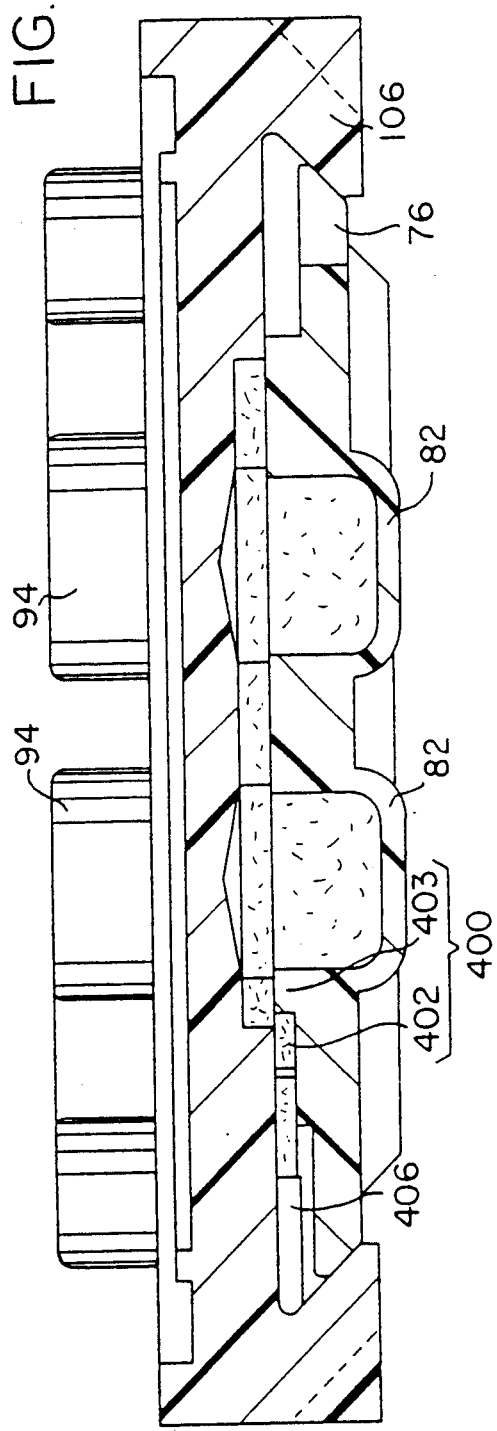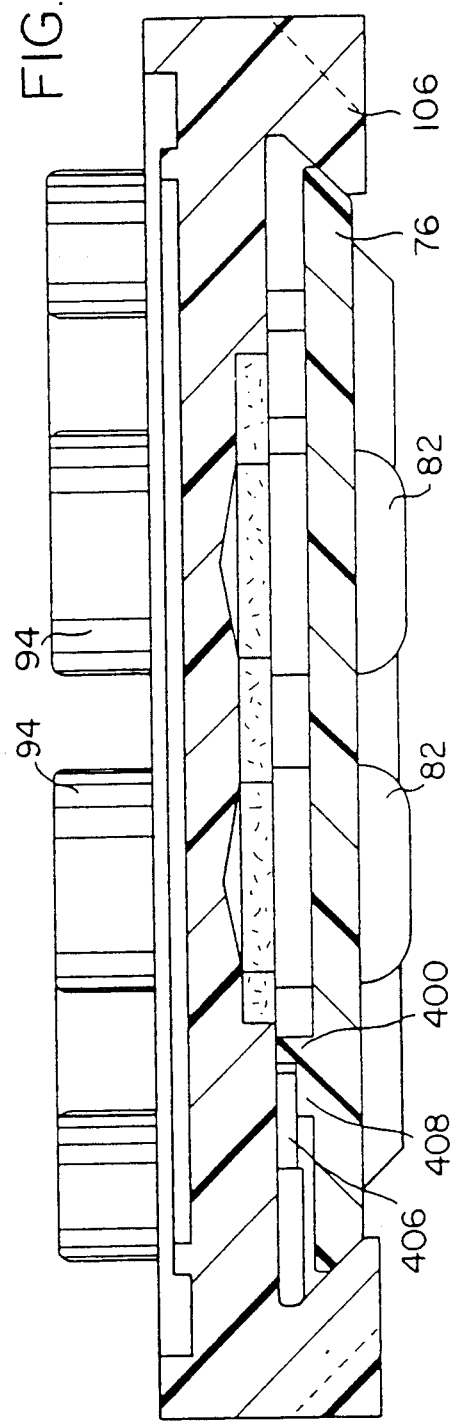

APPARATUS FOR RECEIVING A TEST SPECIMEN AND REAGENT

CROSS-REFERENCE TO RELATED APPLICATIONS

This application is a continuation-in-part of application Ser. No. 043,113, filed Apr. 27, 1987, for "Apparatus for Receiving a Test Specimen and Reagent," now U.S. Pat. No. 4,818,493 which is a division of application Ser. No. 793,376 filed Oct. 31, 1985, for "Analytical Apparatus," now U.S. Pat. No. 4,695,430, which is incorporated herein by reference.

BACKGROUND OF THE INVENTION

U.S. Pat. No. 4,695,430 is directed to an apparatus for automatically performing analytical testing of biological fluids. Individual samples to be tested are introduced into sample cells, where they are injected with one or more reagents and the resulting reactions optically observed. The apparatus comprises a memory for storing a number of different test protocols. All of the tests are performed on the test samples within the sample cells.

During the course of analytical testing, the sample cells are transported to various parts of the apparatus. For example, in a typical test, a sample cell may be loaded with sample fluid at one point, transported to another point to receive reagent, and then transported to a third point to be optically scanned.

U.S. Pat. No. 4,695,430 discloses two different types of sample cell. One type is designed to receive biological fluids that do not contain non-fluid components; the other is for receiving biological fluids that contain non-fluid components. The two types of sample cells are identical except that the second type is adapted to function with a filtering mechanism in the apparatus wherein the non-fluid components are removed, leaving only fluid to be tested. The improvement of the present invention is directed to the second type of sample cell.

Both types of sample cell comprise two parts, a body and a slide, slidable relative to each other. The slide comprises reservoirs for holding the sample of biological fluid to be tested and into which test reagents are added. The reservoirs and the slide may be moved relative to the body to one of two positions, depending on whether the sample of biological fluid is being introduced and the reagents are being injected and the reaction observed. Movement from the first position (loading) to the second position (analysis) is called "indexing".

The second type of sample cell is particularly well-suited for receiving whole blood for testing. Testing is done on plasma, however, and not whole blood.

When extracting plasma from whole blood it is largely unpredictable how much plasma will be obtained from a given quantity of whole blood. The hemocrit (or hematocrit) level of a whole blood sample-the percentage of whole blood volume occupied by red cell after centrifugation—may be anywhere from 15% to 70% among samples typically tested. Consequently, it is likely that a given quantity of whole blood will yield an amount of plasma in excess of the capacity of the reservoirs in the slide. When this happens, the excess plasma will tend to overflow and seep out into the gap between the body and the slide. Then, when the sample cell is indexed, the excess plasma will smear between the body and the slide, and surface tension may cause plasma to be drawn out of the reservoir, thus unpredictably varying the volume of plasma actually being tested, rendering analytical results meaningless.

It is an object of the present invention to prevent smearing of plasma between the body and the slide, by shearing the excess plasma from the gap between the body and the slide.

SUMMARY OF THE INVENTION

The present invention is an improved sampling apparatus, or sample cell, for analytical testing of a fluid containing non-fluid components, particularly whole blood.

The sample cell, in its preferred embodiment, is a flat assembly of transparent plastic, about 2.5 cm square. The assembly consists of two pieces that slide relative to one another, a body and a slide. The body is designed so that whole blood filtered into the sample cell will drain through the channels in the body and down into the reservoirs in the slide.

The body of the sample cell comprises two distinct sections. One section comprises a set of fluid-flow channels, which are designed to accept the whole blood filtrate from the filtering means described in the U.S. Pat. No. 4,695,430. These channels in the top surface communicate with channels that pass through the body itself to the reservoirs formed by cavities in the slide. The other section of the body comprises structures adapted for the injection of reagent and for optical observation when the reagent reacts with the plasma in the reservoirs in the slide. The reservoirs are slidably mounted relative to the body so that in the first position, the reservoirs are aligned with the filter channels through which they are filled with plasma to be tested; then they may be slid, or "indexed", into the second position, where they are aligned with the test wells for analysis.

In order to prevent the smearing of excess fluid during indexing, the present invention comprises a fluid-removing means situated between the body and the slide. This means comprises a barrier that is an elongated member projecting from the top surface of the slide (that is, towards the bottom surface of the body, in the space between the body and the slide). The barrier is elongated substantially in the direction of sliding of the slide relative to the body.

Also projecting from the top surface of the slide is a channel, which connects the rim of one of the reservoirs to the barrier. The shape of this channel is such that only an excess of fluid in the reservoir will be conducted through it. The function of the channel is to accept any overflow from the reservoir and direct it to the area between the body and slide on the other side of the barrier. Thus the barrier will act as a "dam" to prevent excess fluid from interfering with the rims of the reservoirs.

Projecting from the bottom surface of the body (that is, towards the top surface of the slide, in the space between the body and the slide) is a wiper, a rib substantially elongated perpendicular to the direction of sliding, and placed adjacent to the barrier on the side opposite that of the reservoirs. The barrier and the wiper are so configured that, when the sample cell is indexed and the slide is moved relative to the body, the wiper will move along the length of the barrier, serving to shear away any fluid being dammed by the barrier.

Thus, the combination of barrier, channel, and wiper serve to prevent an overflow of fluid in the reservoirs smearing between the body and the slide when the sample cell is indexed. The channel conducts excess fluid from the rims of the reservoirs to the space behind the barrier, and the wiper shears this excess plasma generally to the rear of the sample cell when the sample cell is indexed. This fluid-removing combination serves to make the sampling apparatus of the U.S. Pat. No. 4,695,430 more precise and reliable.

DESCRIPTION OF THE DRAWINGS

For the purpose of illustration, there is shown in the drawings a form which is presently preferred; it being understood, however, that this invention is not limited to the precise arrangements and instrumentalities shown.

FIG. 6 is a sectional view of the sample cell taken along line 6—6 in FIG. 5;

FIG. 9 is a sectional view of the sample cell taken along line 9—9 in FIG. 8.

DETAILED DESCRIPTION OF THE DRAWINGS

Figure 1:
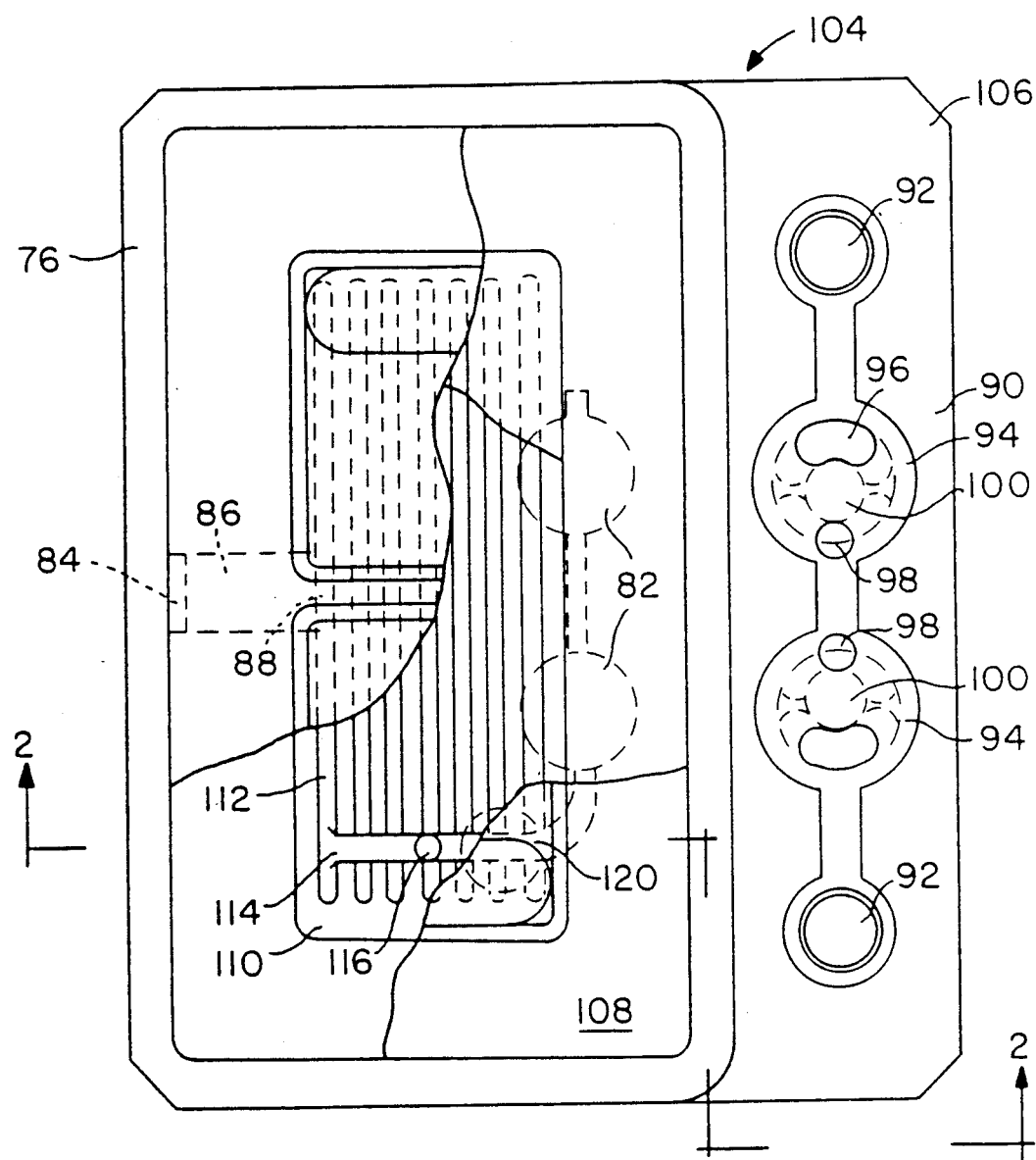
FIG. 1 is a top plan view of the sample cell disclosed and claimed in U.S. Pat. No. 4,695,430.
Figure 2:
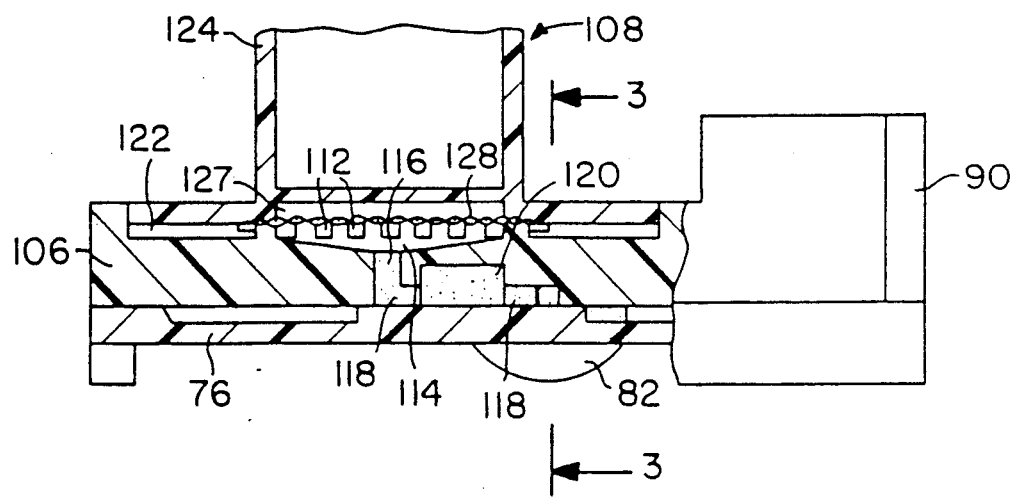
FIG. 2 is a partial sectional view of the sample cell of FIG. 1, taken along line 2—2 in FIG. 1.
Figure 3:
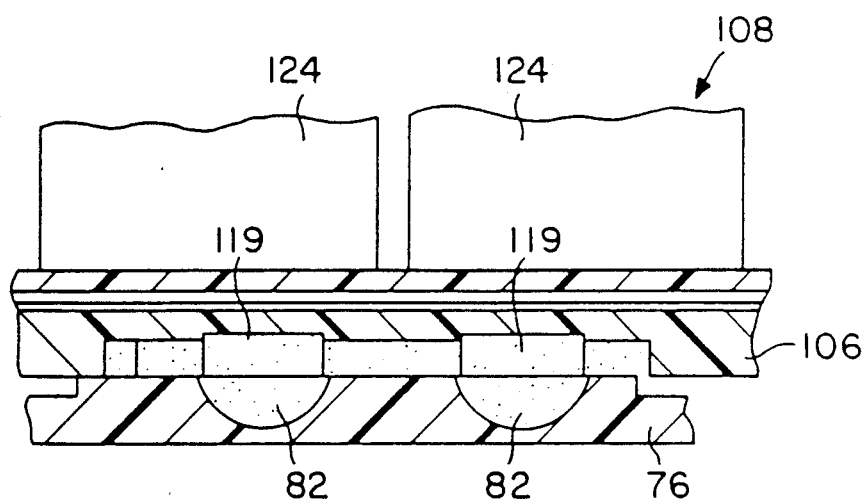
FIG. 3 is a partial sectional view of the sample cell taken along line 3—3 in FIG. 2.

Referring now to the drawings, wherein like numerals indicate like elements, there is shown in FIG. 1 a sample cell 104 for fluids with non-fluid components, referred to in U.S. Pat. No. 4,695,430 as a "whole blood cell." (For ease of reference figures common to the '430 patent and the present invention will be labelled with the same reference numbers.) Sample cell 104 comprises slide portion 76 and body portion 106. Reservoir portion 108 is more fully described in the '430 patent. As explained in the '430 patent, in use body portion 106 is placed on top of slide portion 76, and connects with reservoir portion 108. At the interface between reservoir portion 108 and the plasma collection area 112 of body portion 106 is a filter membrane 128, preferably a polycarbonate sheet having approximately $3 \times 10^7$ pores per square centimeter. The function and operation of reservoir portion 108 and filter membrane 128 is more fully described in the '430 patent, but in brief, reservoir portion 108 comprises two chambers 124 which are closed at the bottom except for openings 126 which are adjacent to the filter membrane 128. The two chambers 124 are alternately pressurized and vented, thus causing the whole blood in the reservoirs 124 to be forced back and forth through openings 126 over filter 128.

As the whole blood is moved back and forth from one reservoir to the other past filter membrane 128, plasma is filtered through the whole blood from filter membrane 128 and collected in channels 112 and 114 of body portion 106.

Body portion 106 comprises molded portion 90 and plasma collection area 110. Plasma collection area 110 comprises a number of longitudinal channels 112 interconnected by and which communicate with a transverse channel 114. Blood plasma that filters through filter membrane 128 is collected in channels 112 and 114. An opening 116 is provided in channel 114 through which collected plasma may flow into wells 82 in slide portion 76. On the underside of body portion 106 beneath the plasma collection area 110, and communicating with opening 116, is plasma channel 118, which conveys the plasma entering opening 116 to wells 82 in slide portion 76. Located in channel 118 is a bubble trap 120 to prevent any bubbles in the collected plasma from being carried into sample wells 82. Body portion 116 also includes cylindrical cavities 119, which act as secondary bubble traps to prevent any trapped air in the collected plasma from reducing the sample volume delivered to sample wells 82, and which also act as excess material traps.

Body portion 106 further comprises a raised molded portion 90, which supports two downwardly opening cylindrical cavities 94, which are substantially open at their bottom end, i.e., the end adjacent slide portion 76. Cylindrical cavities 94 are substantially closed at their opposite (upward) end, with the exception of two openings 96 and 98. Opening 96 permits reagent to be injected into the cavity 94. Opening 98 is a vent opening, which permits air to be vented as reagent is injected. Opening 98 may be eliminated for ease of molding body portion 106, since opening 96 is sufficient for proper venting. Also projecting downwardly from the substantially closed end of cylindrical cavities 94 are light pipes 100, which are used for optical observation of the reaction that occurs when reagent is mixed with the plasma.

In the preferred embodiment, slide portion 76 comprises means defining two generally hemispherical cavities, which form sample wells 82, connected by an intermediate channel 407. Other features of slide portion 76 will be described below.

Figure 4:
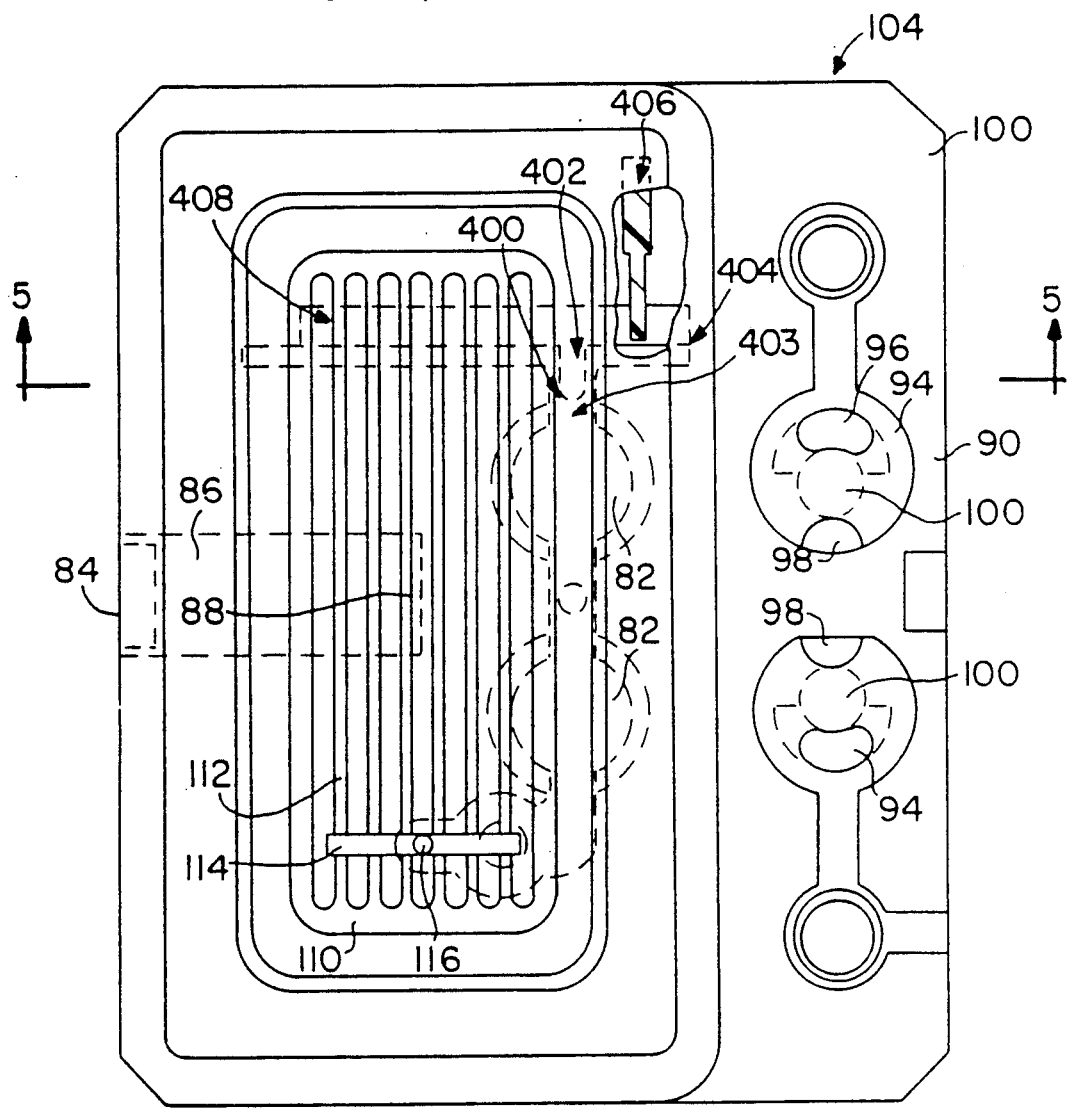
FIG. 4 is a top plan view of an improved sample cell according to the present invention.
Figure 5:
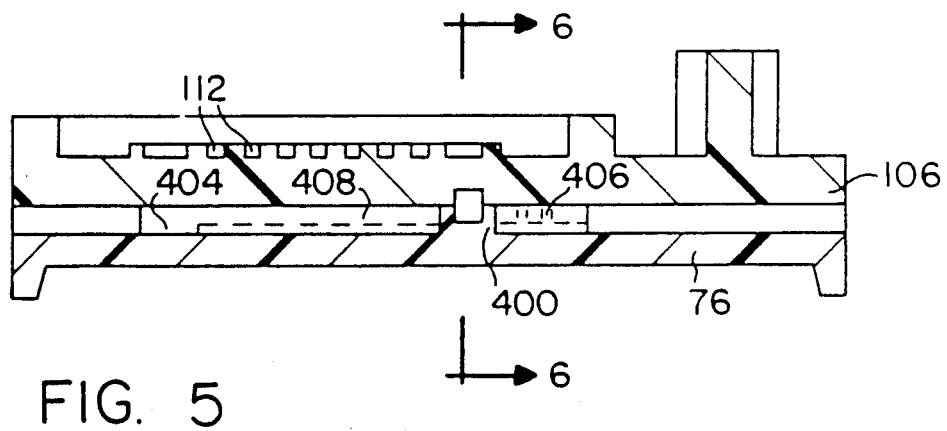
FIG. 5 is a sectional view of the sample cell of FIG. 4 taken along line 5—5 in FIG. 4.
Figure 7:
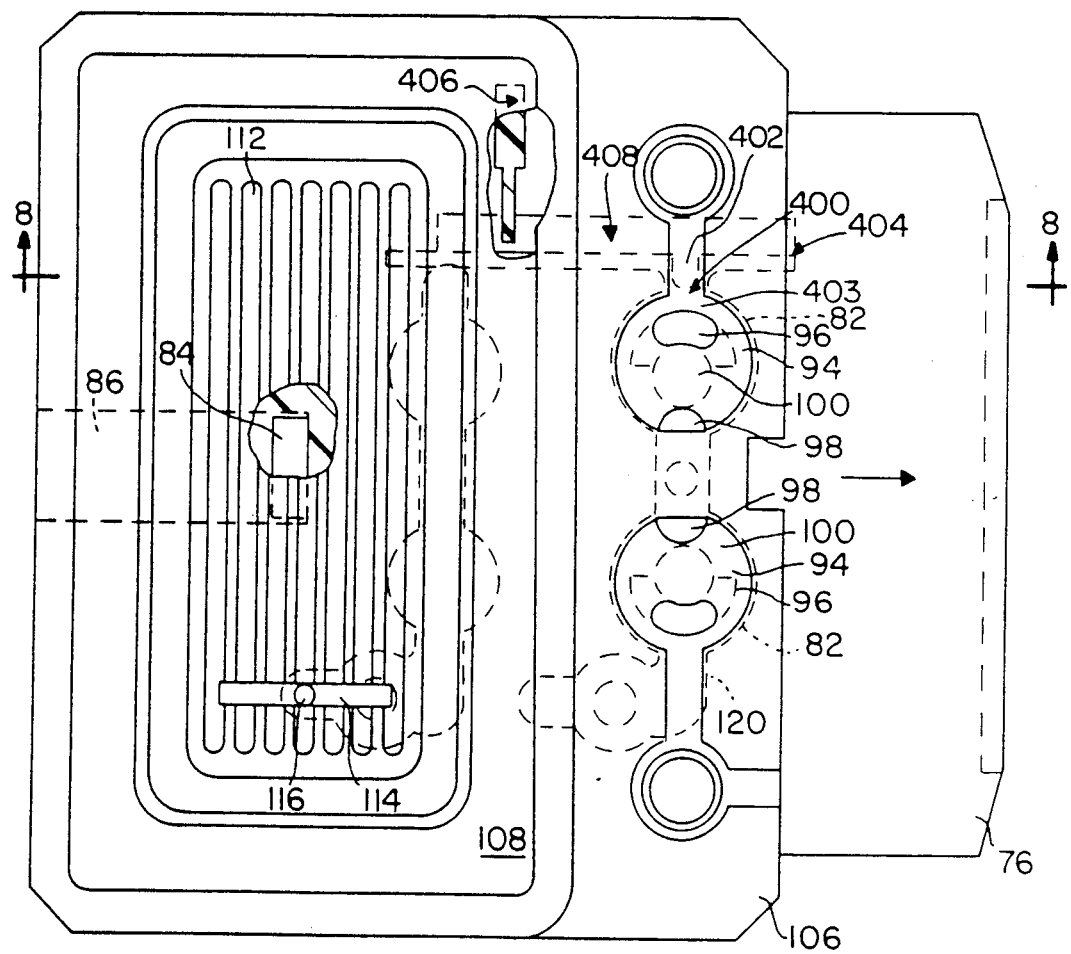
FIG. 7 is a top plan view of the sample cell of the present invention showing the cavities in the slide means aligned with the test cell chambers.
Figure 8:
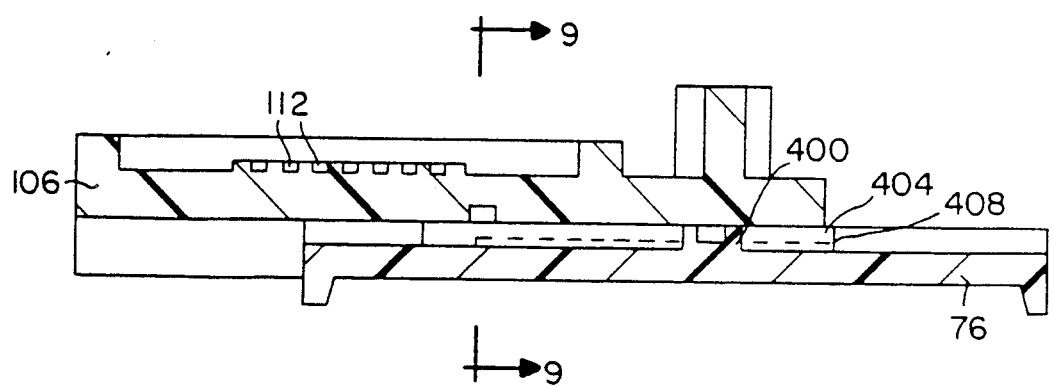
FIG. 8 is a sectional view of the sample cell taken along line 8—8 in FIG. 7.

Body portion 106 and slide portion 76 move relative to each other, within the constraints of stop means 84, 86, 88. Slide portion 76 can be in one of two positions relative to body means 106: the "first position", wherein the wells 82 of slide portion 76 are aligned with channel 118, so that the wells may be filled with the plasma to be analyzed; and the "second position", wherein wells 82 are aligned with the cylindrical cavities 94, so that the plasma-filled wells may be injected with reagent through openings 98 and observed through light pipes 100. The sliding of the slide portion 76 from first to second position is called "indexing". FIGS. 4–6 show the sample cell, incorporating the improvement of the present invention, in the first position; FIGS. 7–9 show equivalent views of the improved sample cell after it has been indexed.

It is upon indexing that the problem the present invention solves occurs. When obtaining plasma from a given quantity of whole blood, it is unpredictable how much plasma will yield. An essential function of wells 82 is to provide for a precise volume of plasma to be tested. When extracting plasma from whole blood, it is likely that an overabundance of plasma will be produced by the filtering process, an amount in excess of the volume of wells 82. When too much plasma is forced into wells 82, the excess tends to overflow into the gap between body portion 106 and slide portion 76. Such an overflow will seriously interfere with the accuracy of the analytical apparatus as a whole. If there is fluid in the gap between body portion 106 and slide portion 76 in the area near the rims of wells 82, liquid adhesion (i.e. surface tension) will cause some plasma to be drawn out of the wells 82, thus varying unpredictably the amount of plasma that will actually be tested. It is crucial, then, to ensure that any overflow is removed from contact with the sample wells 82 or the channel 400, as described below.

The improvement of the present invention is designed to shear away excess plasma from the gap. The improvement comprises a channel 400 which connects one of the sample wells 82 to a barrier means 404. The barrier means 404 is a raised protrusion on the upper surface of slide portion 76, which is substantially in contact with the bottom surface of body portion 106. Barrier means 404 is elongated substantially in the direction of sliding of slide portion 76 relative to body portion 106, and serves as a dam to keep the excess plasma away from the rims of wells 82.

Channel 400, which connects wells 82 to barrier 404, is designed so that only an excess of plasma beyond the volume of wells 82 will spill through to the barrier 404. Thus, the channel 400, in the preferred embodiment, comprises two overlapping cavities, cavity 402, in the slide portion 76 adjacent to barrier 404, and cavity 405, in the form of an indentation in the underside of the body portion 106 (see FIG. 6). Barrier 403 is an extension of barrier 404 and is formed between cavity 402 and the rim of the well 82. When the slide portion is in the first position, cavity 405 is adjacent to barrier 403 and forms a conduit between the rim of well 82 and cavity 402 bypassing barrier 403. In this way an excess of fluid entering well 82 from intermediate channel 407 will have to flow over the top surface of barrier 403, and go through cavity 405 and through cavity 402 to pass beyond barrier 404. Thus no fluid will pass through cavity 405 of channel 400 until the fluid level in well 82 is above the top surface of barrier 403, which sets the proper fluid level in wells 82.

Channel 400 conducts the overflow plasma to the side of barrier 404 opposite that of the wells. Barrier 404, then, serves to collect the excess plasma in one area of the gap between body portion 106 and slide portion 76.

Projecting downward from body portion 106, adjacent to barrier 404, is wiper 406, in the preferred embodiment a shaped rib elongated perpendicularly relative to the barrier, and on the side of the barrier opposite that of wells 82. Wiper 406 is substantially in contact with track 408, a shallow protrusion which projects from the sliding portion alongside barrier 404.

When the sample cell is indexed and slide portion 76 is moved relative to body portion 106 (compare FIGS. 4 and 7) barrier 404 and wiper 406 will move relative to each other in such a way that wiper 406 will sweep through the area between body portion 106 and slide portion 76 on the side of barrier 404 opposite that of wells 82. Thus, the fluid that is dammed by barrier 404 will, when the sample cell is indexed, be sheared to the rear of the cell by the motion of the wiper 406 along barrier 404. Wiper 406 engages track 408 so that the shearing of the fluid beyond barrier 404 will be done cleanly and efficiently.

The present invention may be embodied in other specific forms without departing from the spirit or essential attributes thereof and, accordingly, reference should be made to the appended claims, rather than to the foregoing specifications, as indicating the scope of the invention.

We claim:
1. Apparatus for receiving a sample of fluid to be tested and a test reagent, said fluid containing non-fluid components, and for filtering said non-fluid components from said fluid, comprising:
   (a) slide means having at least one cavity in the top surface thereof for receiving and holding a quantity of filtered fluid to be tested,
   (b) body means slidably engaged with said slide means, said slide means being slidable in a direction between a first position relative to said body means and a second position relative to said body means, the bottom surface of said body means facing the top surface of said slide means,
   (c) said body means having a plurality of fluid flow channels in its top surface and at least one opening therethrough from said channels to the bottom surface of said body means, said opening communicating with said at least one cavity in said slide means when said slide means is in said first position to deliver filtered fluid to said cavity,
   (d) fluid reservoir means located on the top surface of said body means above said fluid flow channels, said fluid reservoir means having two chambers, each chamber being substantially open at its top end and substantially closed at its bottom end except for an opening therethrough, said opening communicating with said fluid flow channels,
   (e) filter means located between said fluid flow channels and said openings in the bottom ends of said fluid reservoir chambers for filtering said non-fluid components from said fluid,
   (f) fluid-removing means for removing fluid from between the top surface of said slide means and bottom surface of said body means, said fluid-removing means comprising:
      (i) barrier means including a member projecting from the top surface of said slide means, said member being substantially elongated in the direction of sliding of said slide means relative to said body means,
      (ii) wiper means including a member projecting from the bottom surface of said body means, said member being substantially perpendicular to said barrier means projecting member,
      (iii) channel means in the top surface of said slide means, extending toward said at least one cavity in said slide means from the side of said barrier means opposite said at least one cavity,
      (iv) said wiper means adapted to shear fluid from the side of said barrier means opposite said at least one cavity when said slide means is moved from said first position to said second position,
   (g) said body means also having at least one downwardly opening chamber therein separate from said fluid reservoir, the lower end of said chamber being in the same plane as the bottom surface of said body means and being substantially open and the upper end of said chamber being substantially closed except for an opening therethrough, said chamber having a downwardly projecting member extending from said upper end of said chamber into said chamber, said chamber being in alignment with said at least one cavity in said slide means when said slide means is in said second position to form a test cell comprising said chamber and said cavity, said member being of a length such that the lowermost end thereof is below the level of the fluid to be tested and reagent in said test cell, and (h) the top surface of said slide means being in sliding contact with the bottom surface of said body means to form means for removing excess fluid to be tested from said at least one cavity as said slide means moves relative to said body means from said first position to said second position to cause a precise accurate volume of fluid to remain in said cavity.

2. Apparatus according to claim 1, wherein the slide means, body means and reservoir means are made from a material transparent to electromagnetic radiation from near-infrared to ultraviolet frequencies.

3. Apparatus according to claim 1, further comprising stop means for preventing over-travel of said slide means from said first position to second position.

4. Apparatus according to claim 1, wherein said filter means comprises a porous polycarbonate sheet.

5. Apparatus according to claim 1, wherein the number of cavities in the top surface of said slide means and the number of said downwardly opening chambers in said body means is equal to two.

6. Apparatus according to claim 1, wherein the fluid flow channels are arranged in parallel rows.

7. Apparatus according to claim 1, wherein said slide means includes means between said slide means and said body means for trapping air bubbles in said fluid to be tested as said fluid is delivered to said cavity.

8. In an apparatus for receiving a sample of fluid to be tested, said apparatus including a first part having a top surface with at least one cavity therein for receiving said fluid and a second part having a bottom surface facing said top surface and being movable in a direction from a first position relative to said first part and a second position relative to said first part, fluid removing means for removing fluid from between said top and bottom surfaces, comprising:

(a) barrier means including a member projecting from said top surface, said member being elongated in the direction of sliding of said slide means relative to said body means;

(b) wiper means including a member projecting from the bottom surface of said body means, said member being substantially perpendicular to said barrier means projecting member, (c) channel means in the top surface of said slide means extending toward said at least one cavity in said slide means from the side of said barrier means opposite said at least one cavity, (d) said wiper means adapted to smear fluid from the side of said barrier means opposite said at least one cavity when said slide means is moved from said first position to said second position.

* * * * *